(12) United States Patent
Alghamdi

(10) Patent No.: US 8,551,187 B1
(45) Date of Patent: Oct. 8, 2013

(54) TOPICAL DEPILATORY AND METHOD OF REMOVING HAIR

(75) Inventor: Saeed Saeed K. Alghamdi, Makkah (SA)

(73) Assignee: UMM Al-Qura University, Makkah (SA)

( * ) Notice: Subject to any disclaimer, the term of this patent is extended or adjusted under 35 U.S.C. 154(b) by 0 days.

(21) Appl. No.: 13/453,861

(22) Filed: Apr. 23, 2012

(51) Int. Cl.
*A61Q 9/04* (2006.01)
*C14C 7/00* (2006.01)

(52) U.S. Cl.
USPC .................................. 8/161; 8/94.16

(58) Field of Classification Search
USPC ...................... 8/94.1 R, 94.16, 161
See application file for complete search history.

(56) References Cited

U.S. PATENT DOCUMENTS

| | | |
|---|---|---|
| 7,078,063 B2 | 7/2006 | Kuo |
| 7,794,694 B2 | 9/2010 | Giacomoni et al. |
| 2002/0183248 A1 | 12/2002 | Oldham et al. |
| 2004/0247715 A1 | 12/2004 | Kuo |
| 2006/0002870 A1* | 1/2006 | Giacomoni et al. ............ 424/59 |
| 2011/0232006 A1 | 9/2011 | Smith et al. |
| 2012/0282195 A1* | 11/2012 | Florence et al. ................ 424/59 |

FOREIGN PATENT DOCUMENTS

| | | |
|---|---|---|
| CN | 101190328 A | 6/2008 |
| DE | 34 34 496 A1 | 3/1986 |
| JP | 58-134030 | 8/1983 |
| WO | WO 2011/116781 A1 | 9/2011 |

OTHER PUBLICATIONS

"What is the medicine for permanent hair removal in alternativer medicine", Feb. 1, 2011.*
Beaman-Mbaya "Antibiotic action of Solanum incanum Linnaeus" Antimicrobial Agents and Chemotherapy, Jun. 1976, p. 920-924.*
Ghazanfar et al., "Medicinal plants of Northern and Central Oman (Arabia)", *Economic Botany*, vol. 47, No. 1, pp. 89-98 (1993).

* cited by examiner

*Primary Examiner* — Lorna M Douyon
*Assistant Examiner* — Amina Khan
(74) *Attorney, Agent, or Firm* — Richard C Litman

(57) ABSTRACT

A topical depilatory made from the juice of a ripe fruit of the *Solanum incanum* is provided. In use as a hair removal agent, the juice of the ripe fruit of the *Solanum incanum* is topically applied to a desired region of skin. Preferably, the juice is left on the region of skin for approximately one hour. The juice acts as a natural depilatory agent, and the hair of the region of skin may then be easily removed by combing, rubbing or the like. Preferably, the region is then washed, following the removal of hair therefrom.

3 Claims, No Drawings

TOPICAL DEPILATORY AND METHOD OF REMOVING HAIR

BACKGROUND OF THE INVENTION

1. Field of the Invention

The present invention relates to hair removal, and particularly to a topical depilatory and method of removing hair using parts of, or juice from the ripe fruit of, the *Solanum incanum*.

2. Description of the Related Art

A depilatory is a cosmetic preparation used to remove the hair from the skin on the human body. Currently, common active ingredients in depilatories include calcium thioglycolate and potassium thioglycolate, both of which break down the disulphide bonds in keratin and weaken the hair so that it is easily scraped off where it emerges from the hair follicle. This break down reaction is affected by the calcium hydroxide or the potassium hydroxide (both alkali). The resulting combinations of calcium hydroxide or potassium hydroxide and thioglycolic acid are calcium thioglycolate (CaTG) or potassium thioglycolate (KTG). The calcium hydroxide or potassium hydroxide is present in excess to enable the thioglycolic acid to react with the cystine present in hair protein.

As the epidermis is also rich in keratin, the skin may become irritated and sensitive if the preparation is left on for too long. This is why chemical depilatories are used primarily for the arms and legs, and should not be used on the face. Further, such chemical depilatories typically are only effective for short periods, with regrowth occurring within two to five days. Because of the substances used, such chemical depilatories often also have an unpleasant odor. It would obviously be desirable to provide a natural depilatory substance that is long lasting, not damaging to the skin, and does not have an unpleasant odor associated with its use.

Thus, a topical depilatory and method of removing hair solving the aforementioned problems is desired.

SUMMARY OF THE INVENTION

The topical depilatory is made from the juice of a ripe fruit of the *Solanum incanum*. In use as a hair removal agent, the juice of the ripe fruit of the *Solanum incanum* is topically applied to a desired region of skin. Preferably, the juice is left on the region of skin for approximately one hour. The juice acts as a natural depilatory agent, and the hair of the region of skin may then be easily removed by combing, rubbing or the like. Preferably, the region is then washed, following the removal of hair therefrom.

These and other features of the present invention will become readily apparent upon further review of the following specification.

DETAILED DESCRIPTION OF THE PREFERRED EMBODIMENTS

The topical depilatory is made from the juice of a ripe fruit of the *Solanum incanum*. In use as a hair removal agent, the juice of the ripe fruit of the *Solanum incanum* is topically applied to a desired region of skin. Preferably, the juice is left on the region of skin for approximately one hour. The juice acts as a natural depilatory agent, and the hair of the region of skin may then be easily removed by combing, rubbing or the like. Preferably, the region is then washed, following the removal of hair therefrom.

The plant *Solanum incanum* is a species of nightshade that is native to northwestern Africa and the Middle East. *Solanum incanum* is commonly referred to by the names "Thorn Apple" and "Bitter Apple". The *Solanum incanum* is a shrub, typically growing up to 120 cm tall. The stems and branches are a yellowish-green with dense stellate tomentum, and are relatively prickly. The leaves of the *Solanum incanum* vary between a length of approximately 3.5 cm and 8.0 cm, and a width between approximately 2.5 and 6.5 cm. The leaves are commonly ovate, sinuate, and are typically densely covered with a grayish-green stellate, along with veins with a few prickles.

The *Solanum incanum* is further characterized by peduncles, which are typically between 10 and 20 mm long, and are often paired. One penduncle bears bisexual flowers and the other bears a short raceme of typically three to five male flowers. The flowers are generally a purple-blue in hue. The fruit of the *Solanum incanum* begins as a yellow immature fruit. As the fruit matures, it turns green, and eventually becomes black.

All ripe (green) and unripe parts of the *Solanum incanum* contain steroid glycosides, in the form of glycoalkaloids. The glycoalkaloids are widely regarded as defensive allelochemicals of the plants against pathogens and predators. They are commonly used instead of the steroidal sapogenin diosgenin as raw material for the industrial production of corticoids. The main steroid alkaloids found in the *Solanum incanum* are solanin (aglycon solanidin) and solasonine (aglycon solasodine). Both solanin and solasonine consist of an aglycone and are connected mostly with three sugar parts, like a chain. Thus, they are often referred to as solatrioses.

The highest quantities of the steroid alkaloids are found in the fruits and seeds of the *Solanum incanum*. The content of solasodine in the young green fruit is approximately 0.42%. Although antifungal and antibacterial properties have also been found in the ripe (green) fruit juice of the *Solanum incanum*, the inventor has found that the ripe fruit juice may further be used as a topical depilatory.

Experiments were conducted on the topical application of each part of the *Solanum incanum*, including the flowers, the unripe (yellow) fruit, the ripe (green) fruit, the leaves, and the roots. Each part was tested in a wet form, prepared by homogenizing the plant part and applying it topically, and further tested in a dry form, prepared by grinding the plant part and mixing the ground material with water to form a topical paste. Additionally, the combination of all parts together, forming one topical composition, was also tested.

Each individual part was found to be effective in hair removal. First, tested on rats, a significant percentage of hair was found to be easily removed from the rat's body only one hour after application of the topical treatment. After twelve weeks, the hair had grown back without apparent damage to the rat's body or hair. These results were found for each part of the *Solanum incanum* tested, as well as the combination of all parts, prepared in both the wet form and the dry form.

The compositions were also tested on a relatively hairy adult human male's leg, and compared against a conventional chemical depilatory and shaving. After one hour, all hair was removed in the area of treatment with the *Solanum incanum*-based depilatory compositions. After twelve weeks, only a small percentage of hair had grown back in the treated area. The treated area was far smoother (i.e., had less hair growth) than an adjacent area treated with the chemical depilatory. A further adjacent area, which had been shaved with a conventional razor, had full hair growth.

The greatest efficacy in hair removal was found using the juice of the ripe (green) fruit of the *Solanum incanum*, with the second greatest efficacy being found in the combination of all plant parts, prepared using either the dry or wet preparations.

It is to be understood that the present invention is not limited to the embodiments described above, but encompasses any and all embodiments within the scope of the following claims.

I claim:

1. A method of hair removal, comprising the steps of:
topically applying juice of a ripe fruit of *Solanum incanum* to a desired region of skin; and
removing hair from the region of skin.

2. The method of hair removal as recited in claim 1, further comprising the step of leaving the applied juice of the ripe fruit of the *Solanum incanum* on the desired region of skin for approximately one hour prior to the step of removing the hair therefrom.

3. The method of hair removal as recited in claim 2, further comprising the step of washing the region of skin following the removal of hair therefrom.

* * * * *